US009983117B1

(12) United States Patent
O'Connor

(10) Patent No.: US 9,983,117 B1
(45) Date of Patent: May 29, 2018

(54) DEVICES AND SYSTEMS FOR IMAGE-BASED ANALYSIS OF TEST MEDIA

(71) Applicant: Germaine Laboratories, Inc., San Antonio, TX (US)

(72) Inventor: Martin O'Connor, San Antonio, TX (US)

(73) Assignee: Germaine Laboratories, Inc., San Antonio, TX (US)

( * ) Notice: Subject to any disclaimer, the term of this patent is extended or adjusted under 35 U.S.C. 154(b) by 0 days. days.

(21) Appl. No.: 15/611,726

(22) Filed: Jun. 1, 2017

(51) Int. Cl.
| G06K 9/00 | (2006.01) |
| G01N 21/01 | (2006.01) |
| G06T 7/00 | (2017.01) |
| G06T 7/13 | (2017.01) |
| G06T 7/90 | (2017.01) |
| G06T 7/60 | (2017.01) |

(52) U.S. Cl.
CPC .......... *G01N 21/01* (2013.01); *G06T 7/0006* (2013.01); *G06T 7/0008* (2013.01); *G06T 7/13* (2017.01); *G06T 7/60* (2013.01); *G06T 7/90* (2017.01)

(58) Field of Classification Search
None
See application file for complete search history.

(56) References Cited

U.S. PATENT DOCUMENTS

| 5,256,886 | A | * | 10/1993 | Wolf | ..................... | G01N 21/53 |
| | | | | | | 250/228 |
| 5,777,244 | A | * | 7/1998 | Kumagai | ........... | G01N 21/8806 |
| | | | | | | 73/865.8 |
| 6,075,893 | A | | 6/2000 | Brandstetter et al. | | |
| 8,908,937 | B2 | * | 12/2014 | Beck | ........................ | G06T 7/60 |
| | | | | | | 382/128 |
| 2003/0036860 | A1 | * | 2/2003 | Rice | ......................... | G01J 1/08 |
| | | | | | | 702/57 |
| 2003/0187344 | A1 | * | 10/2003 | Nilson | ................... | A01K 1/031 |
| | | | | | | 600/407 |
| 2004/0101954 | A1 | * | 5/2004 | Graessle | ........... | G01N 15/1475 |
| | | | | | | 435/288.7 |
| 2004/0114219 | A1 | * | 6/2004 | Richardson | ............... | G01J 3/10 |
| | | | | | | 359/368 |

(Continued)

OTHER PUBLICATIONS

HRDR 200 Chromatographic Immunoassay Reader [online], [retrieved on Nov. 30, 2017], Retrieved from the Internet: <http://www.cellmic.com/content/rapid-test-solution/hrdr-200-chromato-graphic-immunoassay-reader/>, 19 pages.

(Continued)

*Primary Examiner* — Shervin Nakhjavan
(74) *Attorney, Agent, or Firm* — Carr & Ferrell LLP

(57) ABSTRACT

Devices and systems for image-based analysis of test media are disclosed herein. An example device includes four side panels connected together so as to form a tubular rectangle, a floor panel that covers an opening of the tubular rectangle, the floor panel having a raised test bed that receives a test medium, a top panel that having an optical lens that aligns with the raised test bed when the top panel covers another opening of the tubular rectangle. The optical lens is aligned with an aperture that extends through the top panel. The four side panels, the floor panel, and the top panel forming an optic chamber when joined together. The device also includes a light source that illuminates inside the device.

16 Claims, 10 Drawing Sheets

(56) References Cited

U.S. PATENT DOCUMENTS

| | | | | |
|---|---|---|---|---|
| 2006/0268153 A1* | 11/2006 | Rice | ............ | A61B 5/0059 348/370 |
| 2007/0127940 A1* | 6/2007 | Zaima | ............ | G03G 15/5062 399/53 |
| 2007/0174007 A1* | 7/2007 | Ghosh | ............ | G06F 19/20 702/19 |
| 2008/0302964 A1 | 12/2008 | Shinada et al. | | |
| 2010/0022872 A1* | 1/2010 | Stearns | ............ | A61K 49/0013 600/424 |
| 2010/0118130 A1* | 5/2010 | Harris | ............ | G01N 21/51 348/61 |
| 2012/0106702 A1* | 5/2012 | Feke | ............ | A61B 5/0059 378/63 |
| 2013/0021653 A1* | 1/2013 | Hatzav | ............ | H04N 1/0288 358/474 |
| 2013/0224869 A1* | 8/2013 | Perrett | ............ | G01N 21/6428 436/86 |
| 2015/0124072 A1* | 5/2015 | Wei | ............ | H04N 9/735 348/79 |
| 2015/0241363 A1* | 8/2015 | Tuch | ............ | A61B 5/0077 250/362 |
| 2015/0322443 A1* | 11/2015 | McCarty, II | ............ | B26D 5/06 83/13 |
| 2016/0170197 A1* | 6/2016 | Kenny et al. | ............ | G02B 21/365 348/79 |
| 2017/0183713 A1 | 6/2017 | DeJohn et al. | | |

OTHER PUBLICATIONS

Novarum Mobile Reader [online], [retrieved on Dec. 1, 2017], Retrieved from the Internet: <https://www.novarumdx.com/novarum-mobile-reader/i>, 22 pages.

* cited by examiner

DEVICES AND SYSTEMS FOR IMAGE-BASED ANALYSIS OF TEST MEDIA

FIELD OF THE PRESENT TECHNOLOGY

The present disclosure relates to image-based analysis of test media, and more particularly but not by limitation, to devices and systems that comprise a uniquely designed optical chamber that receives the test media. Images are obtained of the test media, and the images can be processed using various algorithms based on a selected test.

SUMMARY

Various embodiments of the present technology include a device, comprising: a floor panel that covers an opening of the tubular rectangle, the floor panel comprising a raised test bed that receives a test medium, a top panel that comprising an optical lens that aligns with the raised test bed when the top panel covers another opening of the tubular rectangle, wherein the optical lens is aligned with an aperture that extends through the top panel, the four side panels, the floor panel, and the top panel forming an optic chamber when joined together, and a light source that illuminates inside the device.

Various embodiments of the present technology include a system, comprising: an optical chamber device comprising: four side panels connected together so as to form a tubular rectangle, a floor panel that covers an opening of the tubular rectangle, the floor panel comprising a raised test bed that receives a test medium, a top panel that comprising an optical lens that aligns with the raised test bed when the top panel covers another opening of the tubular rectangle, wherein the optical lens is aligned with an aperture that extends through the top panel, the four side panels, the floor panel, and the top panel forming an optic chamber when joined together, and a light source that illuminates inside the optical chamber device; and a computing device comprising a processor and memory, wherein the processor executes instructions stored in the memory to: receive a selection of a test from an application, based on the test, select a testing protocol, receive an image of the test medium obtained through use of the optical chamber device, and process the image with the testing protocol to obtain a test result.

Various embodiments of the present disclosure are directed to a system comprising an optical chamber device comprising: four side panels connected together so as to form a tubular rectangle; a floor panel that covers an opening of the tubular rectangle, the floor panel comprising a raised test bed that receives a test medium; a top panel that comprising an optical lens that aligns with the raised test bed when the top panel covers another opening of the tubular rectangle; the four side panels, the floor panel, and the top panel forming an optic chamber when joined together, and a calibration matrix disposed adjacent to the raised test bed; a light source that illuminates inside the optical chamber device; and a computing device comprising a processor and memory, wherein the processor executes instructions stored in the memory to: receive a selection of a test from an application; based on the test, select a testing protocol; receive an image of the test medium obtained through use of the optical chamber device; and apply a calibration profile for the image capturing device, the calibration profile being created from an image of the calibration matrix obtained using the image capturing device; and process the image with the testing protocol to obtain a test result.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

DETAILED DESCRIPTION

Figure 1A:
FIG. 1B is an exploded, perspective view of an example optical chamber device in combination with FIG. 1A that is an image capturing device.

Generally, the present disclosure is directed to devices and systems that allow a user to obtain images of test media and process the images to determine aspects or attributes of the test media. Examples of test media include pregnancy test strips, reagent strips, urine analysis strips, pH test strips, and any other test media where test results can be determined from analysis of visually detectable features of the test media, such as lines, colors, and so forth.

In some embodiments, an optical chamber device is used to receive the test media. Images of the test media can be obtained using any image capturing device, such as a camera or mobile device. Using an application or service, the images can be transmitted to a service or system that is configured to analyze the images of the test media using a test. Tests of the present disclosure comprise algorithms that when applied to the images output data related to the specific testing procedure selected.

In one embodiment, the optical chamber device is a specially design chamber to be used in conjunction with an image and testing application (hereinafter "App"), as well as a picture analysis software (PAS) contained on a cloud based server.

The optical chamber device can be used in conjunction with the App which is intermediary software that processes an image of a test medium and transfers it to a cloud based server that executes the PAS. In some embodiments, the PAS uses algorithms, designs, and functions to critically analyze the images of test media. Results are transmitted back to the requesting device electronically.

As mentioned above, the present disclosure provides systems and devices that allow for testing of many types of testing media, such as cassettes, strips and midstream devices that produce visually distinct results. Examples of visually distinct results include colored lines, such as tests for pregnancy, microorganisms, and so forth. Other examples of test that include visually distinct results include are colored pads, such as urinalysis strips, glucose strips, water test strips, and so forth. Additional examples of test that include visually distinct results include colored tablets, such as those used for testing ketones, bilirubin, and other biochemical attributes. Thus, the present disclosure can be used for test media used in many different technological fields such as medical, agricultural, environmental, food safety, water, animal health, and so forth—just to name a few.

Advantageously, the devices and systems of the present disclosure allow for standardization in image capturing and processing of images for interpreting test media regardless of the capabilities of the image capturing device used. That is, various image capturing devices can obtain images at different resolution levels or can cause images to be captured with differing image properties, such as hue, saturation, clarity, and so forth, relative to one another. The systems and methods of the present disclosure can utilize calibration features to standardize and/or correct images obtained from a wide variety of image capturing devices, ensuring that variability in image capturing devices capabilities do not affect test media image processing.

These and other advantages of the present disclosure are provided herein with reference to the collective drawings.

Figure 1B:
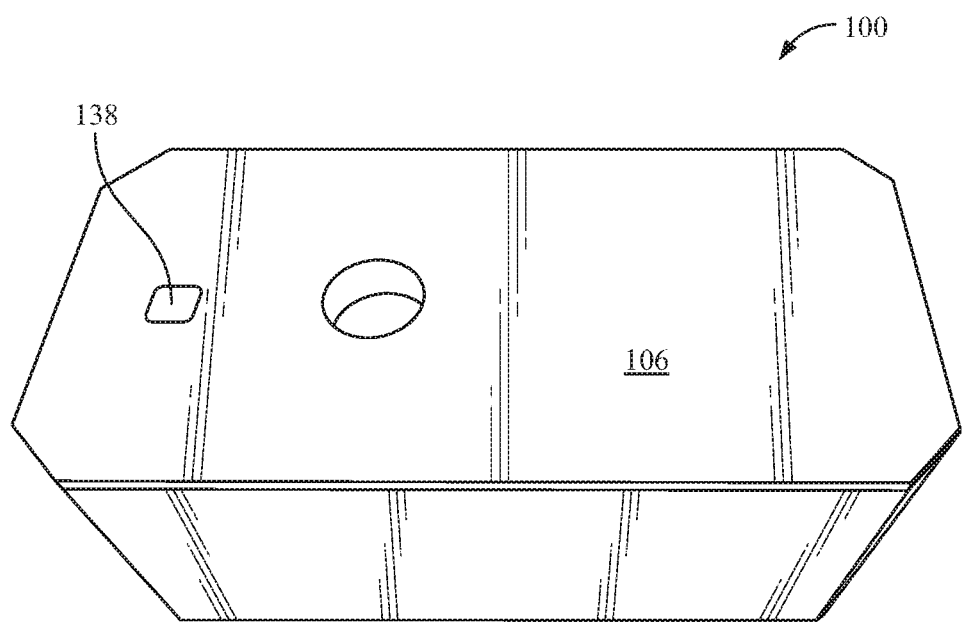

FIG. 1B is an exploded, perspective view of an example optical chamber device 100 in combination with an image capturing device 101 in FIG. 1A. The optical chamber device (hereinafter "device 100") is an enclosure that generally comprises four side panels (see FIG. 2). A floor panel 104 (see FIG. 3) and top panel 106 are also incorporated.

Figure 2:
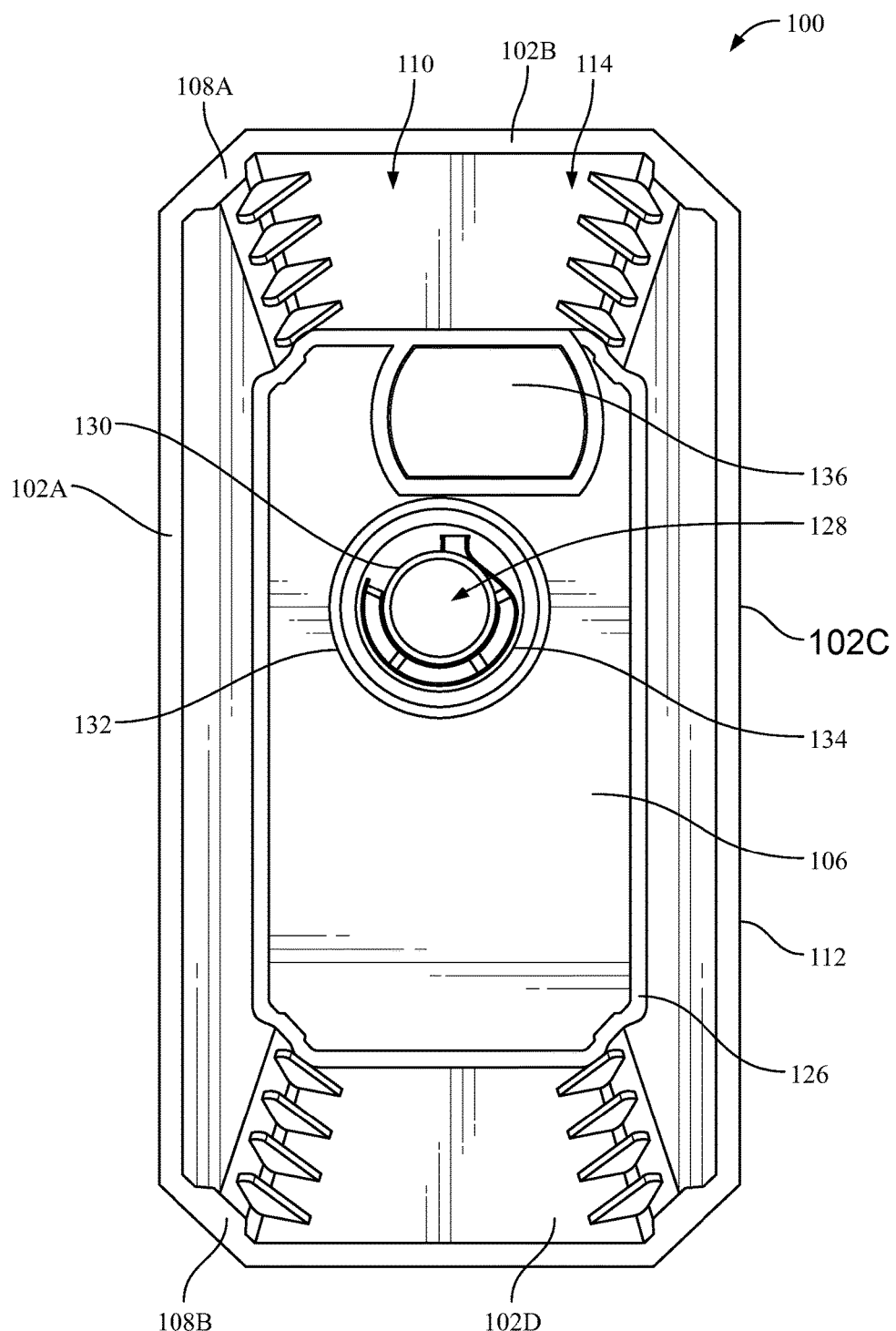
FIG. 2 is a perspective view of a portion of the example optical chamber device of FIG. 1B.

Referring to FIG. 2, according to some embodiments, four side panels 102A-D are connected together so as to form a tubular rectangle. The four side panels 102A-D can be created as an integrated or monolithic device. In other embodiments the side panels 102A-D can be selectively connected together and separated as desired.

The device 100 can be manufactured from any suitable material that would be known to one of ordinary skill in the art with the present disclosure before them. In some embodiments, the panels of the device 100 are manufactured from an opaque thermoplastic polymer such as a white acrylonitrile butadiene styrene, which absorbs very little light to enhance the lighting environment within the device 100.

In some embodiments, each of the side panels 102A-D comprises angled ends, such as angled ends 108A and 108B of side panel 102A. In some embodiments, the angled ends are configured to interlock or interface with angled ends of adjacent side panels. For example, the angled end 108A of side panel 102A can interlock or join with the angled end of side panel 102B, and angled end 108B of side panel 102A can interlock or join with the angled end of side panel 102D. In one example embodiment the side panels 102A-D can be configured with tongue and groove interlocking. For example, side panel 102A can include a tongue and side panel 102B can include a groove that receives the tongue.

According to some embodiments, faces of the side panels 102A-D that are inward facing when the side panels 102A-D are joined together can be coated with a reflective material. The reflectivity of the material is selectable based on design criteria, such as test media analyzed and capabilities of the image capturing device used in conjunction with the device 100.

According to various embodiments, the side panels 102A-D can each comprise a series of brackets, such as brackets 110. The brackets on each of the side panels 102A-D are in planar alignment such that the floor panel 104 (FIG. 3) can be placed in differing proximity relative to the top panel 106.

The when the side panels 102A-D are joined with the floor panel 104 (FIG. 3) and the top panel 106, they cooperatively define an illumination volume of the device 100. The illumination volume is selectable based on the placement of the floor panel 104 relative to the top panel 106. When the floor panel 104 contacts and covers a lower edge 112 of the device 100, the illumination volume is a maximum size.

As the floor panel 104 is selectively placed on different brackets, the floor panel 104 can be disposed in closer proximity to the top panel 106. This placement of the floor panel 104 in closer proximity to the top panel 106 reduces the illumination volume from its maximum size. This selectable variability in the illumination volume allows for testing of test media in optical chambers of varying size. For example, some tests require execution in volumes that are smaller than other tests which require execution in larger volumes. In other instances, the selectivity in volume size is desirable when differing types of image capturing devices are used, specifically when the image capturing devices have different focal lengths that may not be adjustable.

Figure 3:
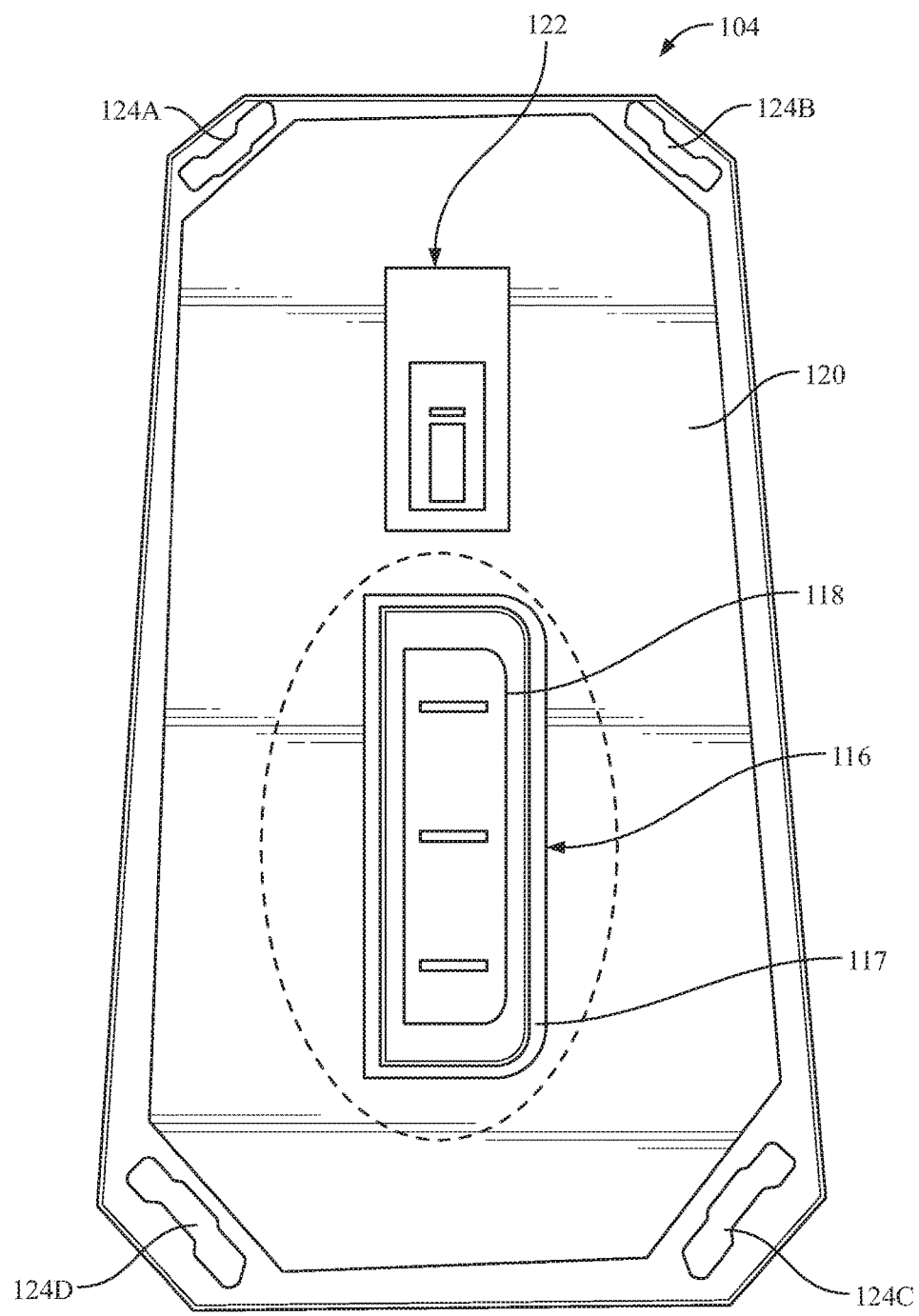
FIG. 3 is a perspective view of an example floor panel of the example optical chamber device of FIG. 1B.

Referring now to FIG. 3, according to some embodiments, the floor panel 104 covers (or is inserted within when using the brackets) an opening 114 (see FIG. 2) of the tubular rectangle, which is defined by the lower edge 112. The floor panel 104 comprises a test bed 116 that receives a test medium 118. The floor panel 104 can also comprise a reflective coating that is applied to an inward facing surface 120 that faces the top panel 106 when the floor panel is joined to the side panels 102A-D.

In some embodiments, the test bed 116 is raised relative to the remainder of the inward facing surface 120. The test bed 116 is defined by a raised template outline 117 that is specifically contoured for a shape of the test medium 118 to provide accurate orientation and position when using the App and PAS system.

In some embodiments, the floor panel has one raised template design on one side and a different raised template design on the opposite side, which allows for double designs for each floor panel. Each of the raised templates receives a specific type of test medium. In some embodiments, this allows two test mediums to be analyzed at the same time. For example, two reagent strips can be obtained to test the same condition of a patient. Rather than relying on a single test medium, the PAS can analyze the two reagent strips together and determine similarities and differences therebetween.

In various embodiments, the floor panel 104 can comprise a calibration matrix 122 that is disposed above the test bed 116. The calibration matrix 122 can be utilized to calibrate the image capturing device and/or calibrate the PAS system using images obtained of the calibration matrix 122. The PAS can use calibration algorithms to process the portion of the image that includes the calibration matrix 122. The image can include both an image of the test medium 118 and an image of the calibration matrix 122. In other embodiments, an image of the calibration matrix 122 can be obtained prior to imaging the test medium 118 and processed to calibrate the system and/or the image capturing device.

In one or more embodiments, the floor panel 104 can comprise protrusions 124A-D that fit into a tubular opening created when the side panels 102A-D are joined together.

Referring back to FIG. 2, the top panel 106 comprises a substantially flat member that is configured to cover an opposing end of the device 100 relative to the floor panel 104. In some embodiments, the top panel 106 comprises a raised flange 126 that is inserted into the space created between the side panels 102A-D when they are joined to create a rectangular tube. The raised flange 126 ensures that light does not escape from the device 100 when in use.

In some embodiments, the top panel 106 comprises an aperture or optical lens 128 that provides an opening that aligns with the lens of an image capturing device, as will be described in greater detail below. In some embodiments, the aperture 128 is surrounded by an inner circular flange 130 and an outer circular flange 132 that is larger and concentric with the inner circular flange 130. A light source 134 can be disposed in an annular spacing created by the inner circular flange 130 and the outer circular flange 132. In some embodiments, the light source 134 comprises a plurality of light emitting diodes (LEDs). An enclosure 136 receives and retains a power source, such as batteries that provide power to the light source 134. In some embodiments, the light source 134 is controlled through a switch 138 (see FIG. 1B) that is accessible on an upper surface of the top panel 106.

Lighting is optimized for the device 100 to produce an optimal environment for obtaining accurate results using the App and PAS. In one embodiment four LEDs are used that produce approximately 26 lumens. In another scenario, 18 LEDs are used that produce approximately 120 lumens.

As noted above, light within the device 100 is enhanced by the use of reflective material. In one embodiment, only the floor panel 104 is covered with reflective material to reflect light upwardly towards the top panel 106. In some versions, all inside panels of the device 100 are covered with a reflective material to reflect light inside the device 100.

Figure 4:
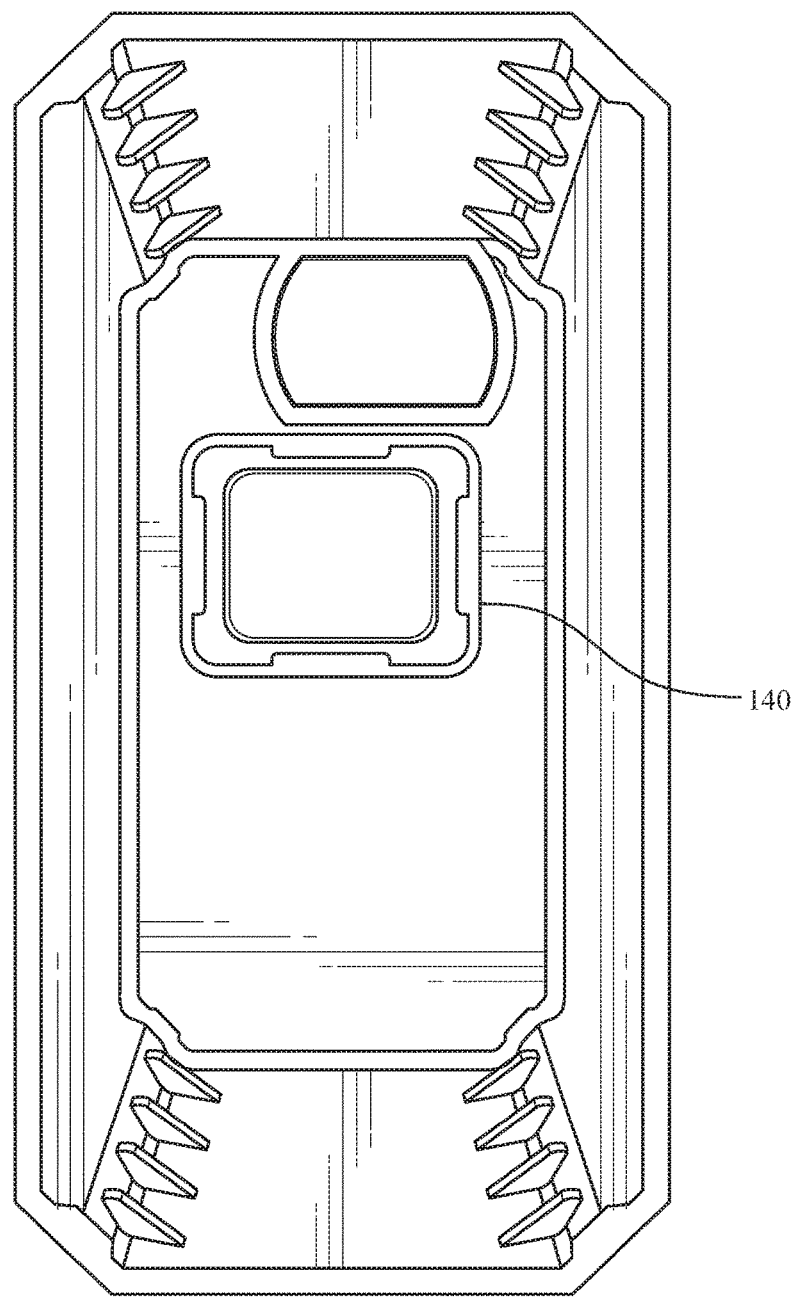
FIG. 4 is a perspective view of another example top panel for use with the device of FIG. 1B.

In one or more embodiments, the aperture 128 aligns with the raised test bed 116 of the floor panel 104 when the top panel 106 is installed on the device 100. In some embodiments, an optical lens can be associated with the aperture 128. For example, special purpose lenses can be incorporated into the device 100 to enhance the accuracy of certain test media results. In one embodiment, a macro lens can be incorporated into the aperture 128 when the test medium exhibits results that are physically smaller or when the lens improves accuracy. In another embodiment, a colored lens can be incorporated to enhance certain test medium results, such as red, blue or polarizing lenses (see FIG. 4, lens 140).

Figure 5:
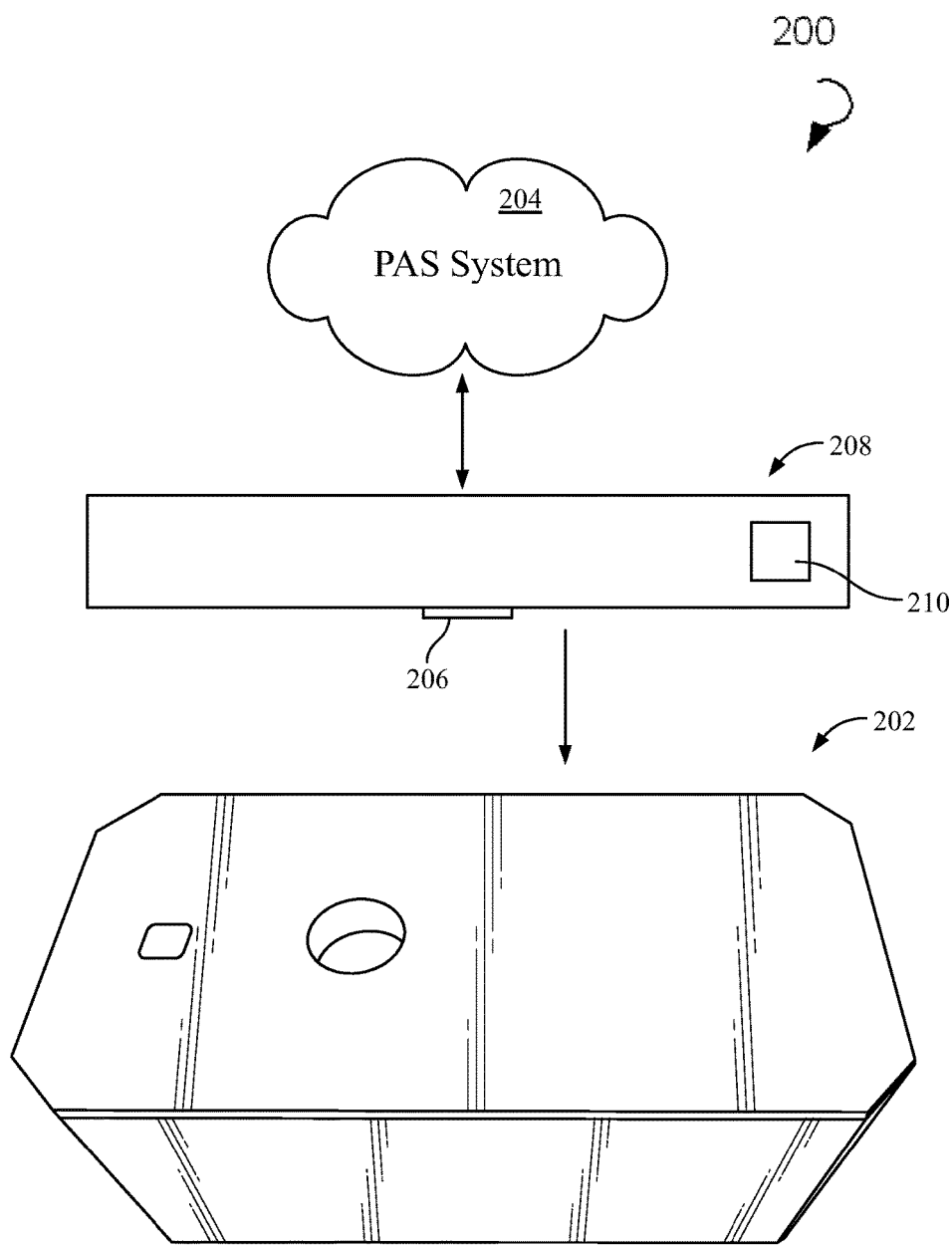
FIG. 5 is a schematic diagram of an example embodiment of a system that can be used to practice aspects of the present disclosure.

FIG. 5 is a schematic diagram of an example embodiment of a system that can be used to practice aspects of the present disclosure. The system 200 comprises an optical chamber device 202, a PAS system 204, and an image capturing device 206.

In some embodiments, the optical chamber device 202 can comprise, for example, the optical chamber device 100 of FIGS. 1-4. The image capturing device 206 can comprise any image capturing device that would be known to one of ordinary skill in the art such as a camera or mobile device equipped with a camera. The image capturing device 206 could include a computing device such as a mobile device 208. The mobile device 208 can execute an application "App 210" that is used to select a test. For example, the App 210 can provide the user with a list of tests that can be performed for the test medium being analyzed. In some embodiments, the PAS system 204 can determine a test type from image identification of the test medium. For example, an image can be obtained of the test medium. The PAS system 204 can process the image to determine what type of test medium is in the image. A test or list of test is selected based on the image analysis. In some embodiments, the user can confirm the selected test. Test results can be delivered back to the mobile device 208 through the App 210.

The PAS system 204 can include, for example, a cloud-based computing environment or server that is configured for image processing in accordance with the present disclosure. The PAS system 204 can provide image processing services such as calibration and test medium evaluation.

In general, the PAS system 204 receives images obtained by the image capturing device 206 of the optical chamber device 202. The PAS system 204 applies various algorithms to optionally calibrate for subsequent image processing, as well as perform image analysis and generate test results from image analyses of test media.

With respect to calibration, the specially designed calibration matrix has been developed that standardizes image capturing device 206 with the optic chamber device 202 and the cloud based PAS system 204. As noted above, the calibration matrix is included in the floor panel (such as calibration matrix 122 of FIG. 3). Upon initial use and at appropriate intervals, the calibration matrix is used to ensure proper results from images obtained of the test medium.

Figure 6:
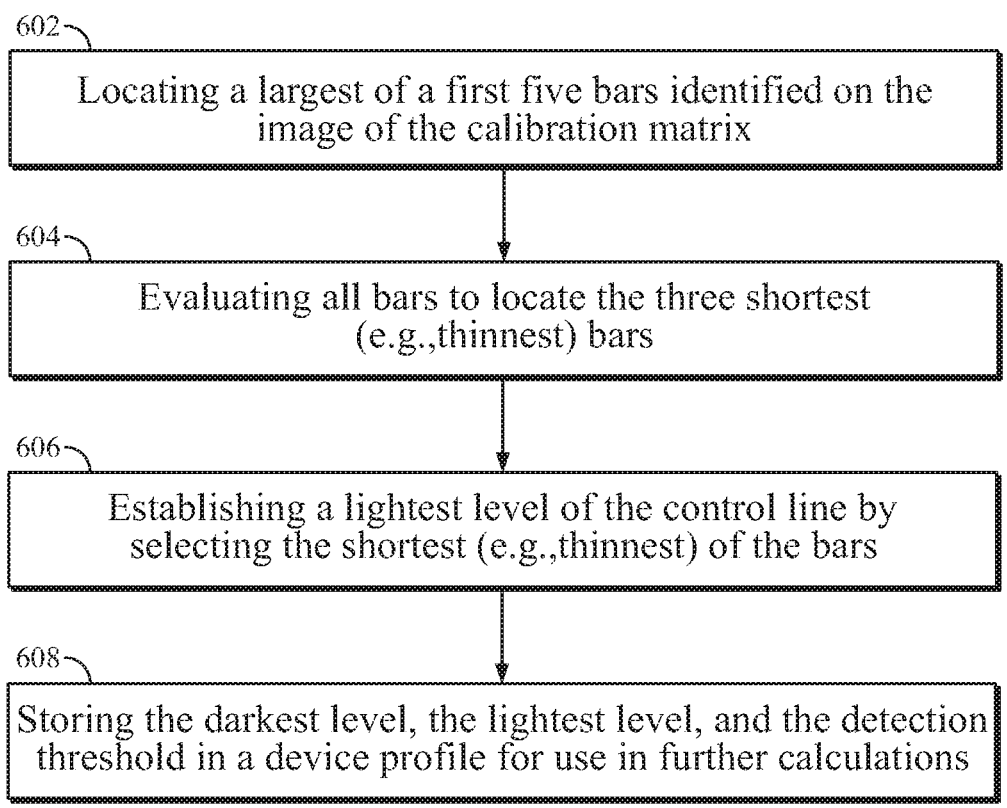
FIG. 6 illustrates a flowchart of an example method for calibration.
Figure 7:
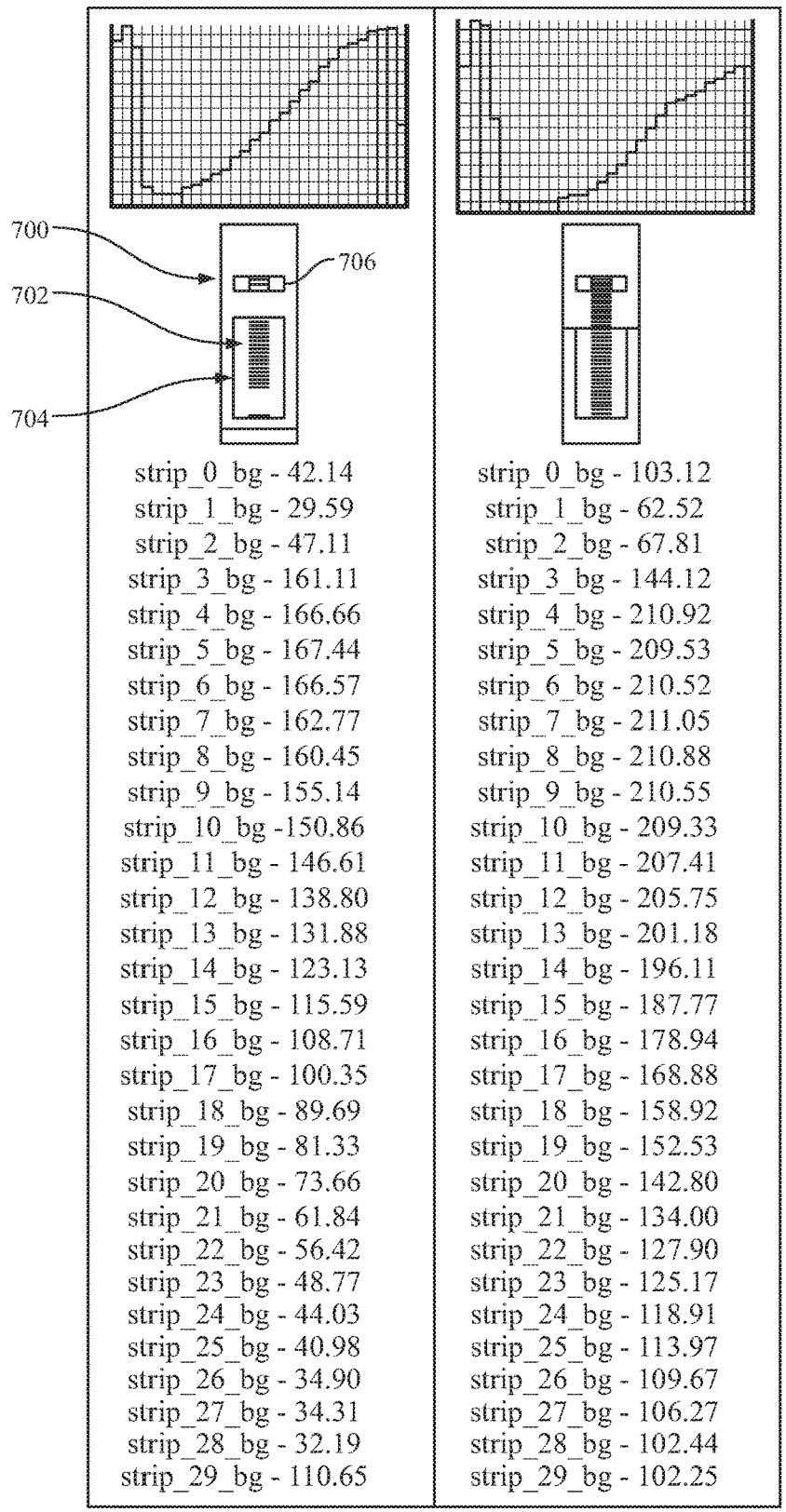
FIG. 7 illustrates example graphical representations created from images processed of a calibration matrix.

FIG. 6 illustrates a flowchart of an example method for calibration. FIG. 7 illustrates example graphical representations created from images processed of a calibration matrix. Turning briefly to FIG. 7, the calibration matrix 700 comprises a series of bars 702 that are arranged into a vertical configuration. The series of bars 702 includes a darker area 704 towards a bottom of the calibration matrix. The series of bars 702 are progressively lighter towards a higher end of the calibration matrix. A control line 706 is disposed above the series of bars 702. Variances in how this calibration matrix 700 is captured by the image processing device can be used to calibrate the image processing of images obtained by the image processing device. For example, one image processing device may have poorer exposure of dark areas of images compared to other image processing devices. These differences can lead to errors in image processing if these differences are not accounted for through calibration.

The method of FIG. 6 generally includes a step 600 of converting an image of the calibration matrix (such the image of the calibration matrix 700 in FIG. 7) into an array of values that correspond to the series of bars 702.

The method of FIG. 6 includes a step 602 of locating a largest of a first five bars identified on the image of the calibration matrix. The largest (e.g., thickest) bar is established as a darkest level (darkest level control line), which is referred to also a control line. Next, in step 604, the method of FIG. 6 includes evaluating all bars to locate the three shortest (e.g., thinnest) bars. The PAS system 204 then finds the thickest and thinnest of the bars. A difference between the thickest and thinnest of the bars is set as a detection threshold.

The method of FIG. 6 then includes a step 606 of establishing a lightest level of the control line by selecting the shortest (e.g., thinnest) of the bars from step 604. The method of FIG. 6 then includes a step 608 of storing the darkest level, the lightest level, and the detection threshold in a device profile for use in further calculations.

In FIG. 7, a graphical representation of the calibration matrix 700 is displayed. A graphical representation is created based on an array of values. That is, for each of the series of bars 702 of the calibration matrix 700, a value is calculated related to a darkness of the series of bars 702.

After calibration, in some embodiments, an image is captured by an image capturing device and transmitted to a PAS system. The control line (darkest line) is then detected by the PAS system. When detected, an array of bars is created descending from the control line. A width, height, and count (e.g., location) of the control line bar can be controlled to achieve optimum samples. The various components are then determined such as lightest line and detection threshold. Using this information, the image of the test medium is processed to detect positive or negative results, create graphical representations of the array created, and calculate quantified results.

In some embodiments, a set of algorithms utilized by the PAS system analyzes images by subtracting background noise, selecting signal bands, plotting pixel density ratios of the bands and measuring the area underneath each peak to provide quantitative and qualitative results.

As mentioned above, a self-calibration method can be performed by the PAS system and incorporated in image analysis processes to compensating for the background color of a membrane of a test medium and for camera variances between smartphones, tablets or other mobile devices—just to name a few.

Referring now to FIGS. 8A-8C and 9 collectively, which describe and illustrate an example image processing method executed by the PAS system.

Figure 8A:
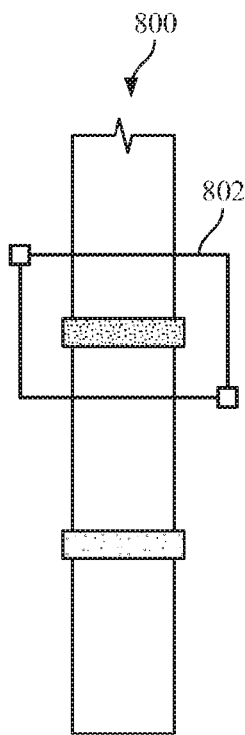
FIGS. 8A-C illustrate cropped images of a test medium.
Figure 8B:
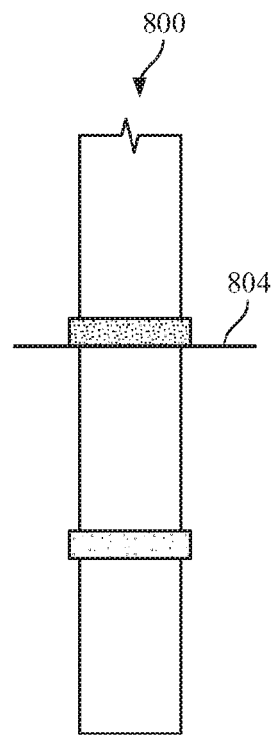
Figure 8C:
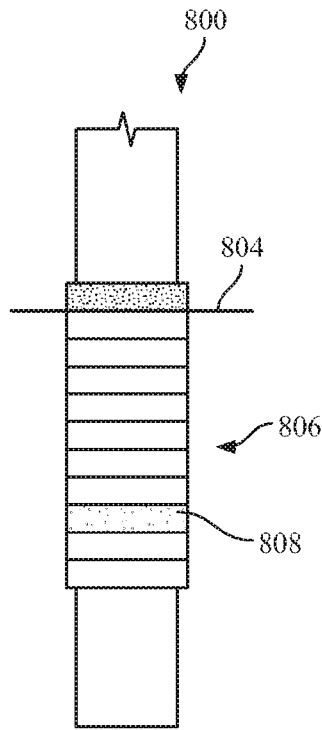
Figure 9:
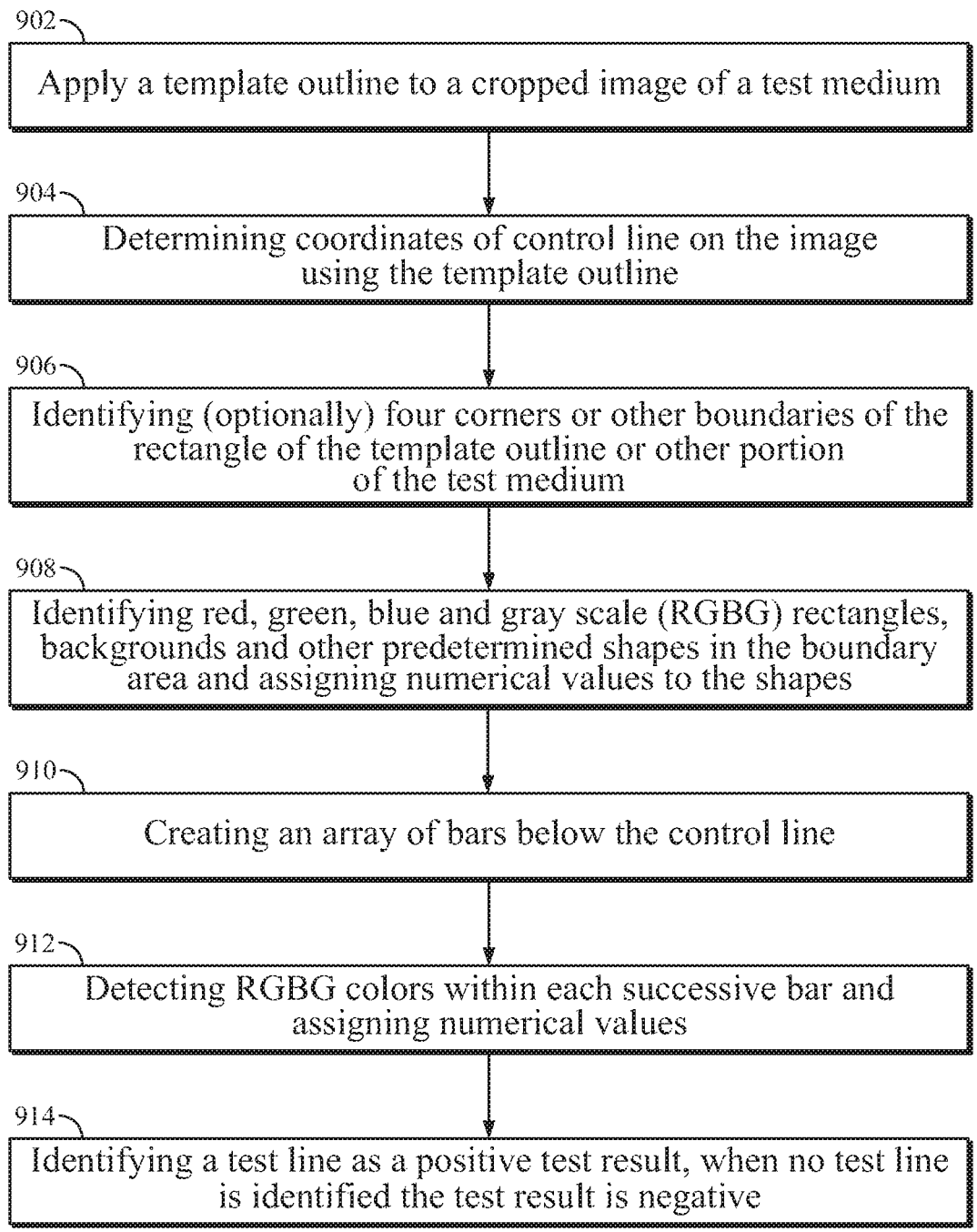
FIG. 9 is a flowchart of an example method for processing images of the test medium of FIGS. 8A-C.

In more detail, an App installed on a mobile device can be used to apply a template outline 802 to a cropped image of a test medium 800, as illustrated in FIGS. 8A-C, in step 902. For example, a pre-determined rectangular field (e.g., template outline 802) is coordinated to align with the test medium 800 located within the optic chamber device. The template outline 802 can be changed to accommodate many specific test media with different shapes and sizes, which also may require different testing specifications.

In one or more embodiments, coordinates of a control line (see 804 of FIG. 8B) on the test medium when positioned in the optic chamber device (which includes the raised template outline on the floor panel) are determined using the template outline 802 in step 904. The PAS system then searches within template outline 802 identifying the four corners of any rectangle, which in one specific scenario is the control line of the test medium, in a step 906. The PAS system can identify the control line anywhere within the template outline 802.

The PAS system then identifies red, green, blue and gray scale (RGBG) rectangles, backgrounds and other predetermined shapes and assigns numerical values to the shapes in step 908.

According to some embodiments, the PAS system then creates an array of bars (see 806 of FIG. 8C) going down from the control line in step 910. To be sure, a width, height and count of bar is controlled by PAS system achieve best quality of samples.

The PAS system can then detect RGBG colors within each successive bar and assign numerical values in step 912. As each successive bar is assign numerical values, the PAS system identifies if there is a significant increase from previous bars. Any bar containing a significant increase means a "test line" has been identified, such as test line 808. What constitutes a "significant increase" can be established through empirical testing or other design requirements. The method includes identifying a test line as a positive test result and when no test line is identified the test result is negative in step 914.

Again, this process can be adjusted through use of the calibration factors described in greater detail above.

In an example use case, an optical chamber device is assembled by sequentially snapping the four vertical sides together. A top panel is snapped on top of the four vertical sides. A floor panel is placed underneath the four vertical sides with the template aligned directly underneath the window opening.

A smartphone, tablet or mobile device is placed on top of the optic chamber with the camera lens viewing through the window opening. The App installed on the device is opened.

All updated test and calibration data is automatically downloaded in some embodiments. The calibration data has been stored in a device profile that establishes a baseline that standardizes results for each specific user's mobile device (e.g., calibration for the image processing device).

The user then selects a test from the App. In this embodiment, the test selected is a pregnancy test. Next, drops of patient's urine are added to the pregnancy test medium. The test medium is then place the optical chamber device in a specialized corresponding floor panel which accommodates the pregnancy test device. Again, the shape of the test medium corresponds to a shape of the test bed of the optical chamber device for ease of use.

Next, the user aligns the mobile device so the template (e.g., test bed) is aligned with the outline of the pregnancy test medium. A picture is then obtained. In some embodiments, the picture is uniquely cropped by the App and then transmitted via wireless Internet to the PAS system in the cloud.

The PAS system scans the picture to locate and identify four corners of the control line. The PAS system can identify RGBG colors (red, green, blue and gray scale) rectangles and other pre-determined shapes and assigns numerical values.

Upon successful detection of the control line, the PAS system creates an array of bars going toward a potential test line. The PAS system detects RGBG colors within each successive bar and assigns numerical values.

If the PAS system identifies a bar that has a significant increase of RGBG values from a previous bar, this means a test line has been identified, which results in a positive pregnancy test result. RGBG values of the test line can be correlated to provide quantitative results.

If no significant increase of RGDG values from a previous bar is identified, this means no test line has been identified, which results in a negative pregnancy test result. The PAS system creates a graph of the results and transmits the same via wireless internet to the mobile device.

In another use case example, a test medium of a reagent strip is evaluated. The optical chamber creation and calibration steps are the same as described in the prior example use case.

The user can dip the reagent strip (test medium) in the patient's urine. The user then places the reagent strip in the specialized corresponding floor panel which accommodates the reagent strip. The user selects "reagent strip test" within the App.

The user aligns the mobile device so the template is aligned with the outline of the reagent strip test device and obtains an image. The image is cropped and transmitted to the PAS system.

The PAS system scans the picture to locate and identify the four corners of the first reagent pad. The PAS system can identify RGBG colors (red, green, blue and gray scale) rectangles and other pre-determined shapes and assigns numerical values.

Upon successful detection of the first reagent pad, the PAS system creates an array of bars going towards the end of the reagent strip which allows for the detection of additional reagent pads. The PAS system detects RGBG colors within each successive bar (and reagent pads) and assigns numerical values.

The PAS system compares results of the bars (and reagent pads) to known standard results and makes adjustments per the calibration matrix. The RGBG values of the reagent pads are correlated to provide qualitative, semi-quantitative, or quantitative results. Example of results include: (a) glucose is 250 mg/dl; (b) protein is 30 mg/dl; (c) nitrite is 0.1 mg/dl; and (d) leukocytes is 70 cells/μl.

Figure 10:
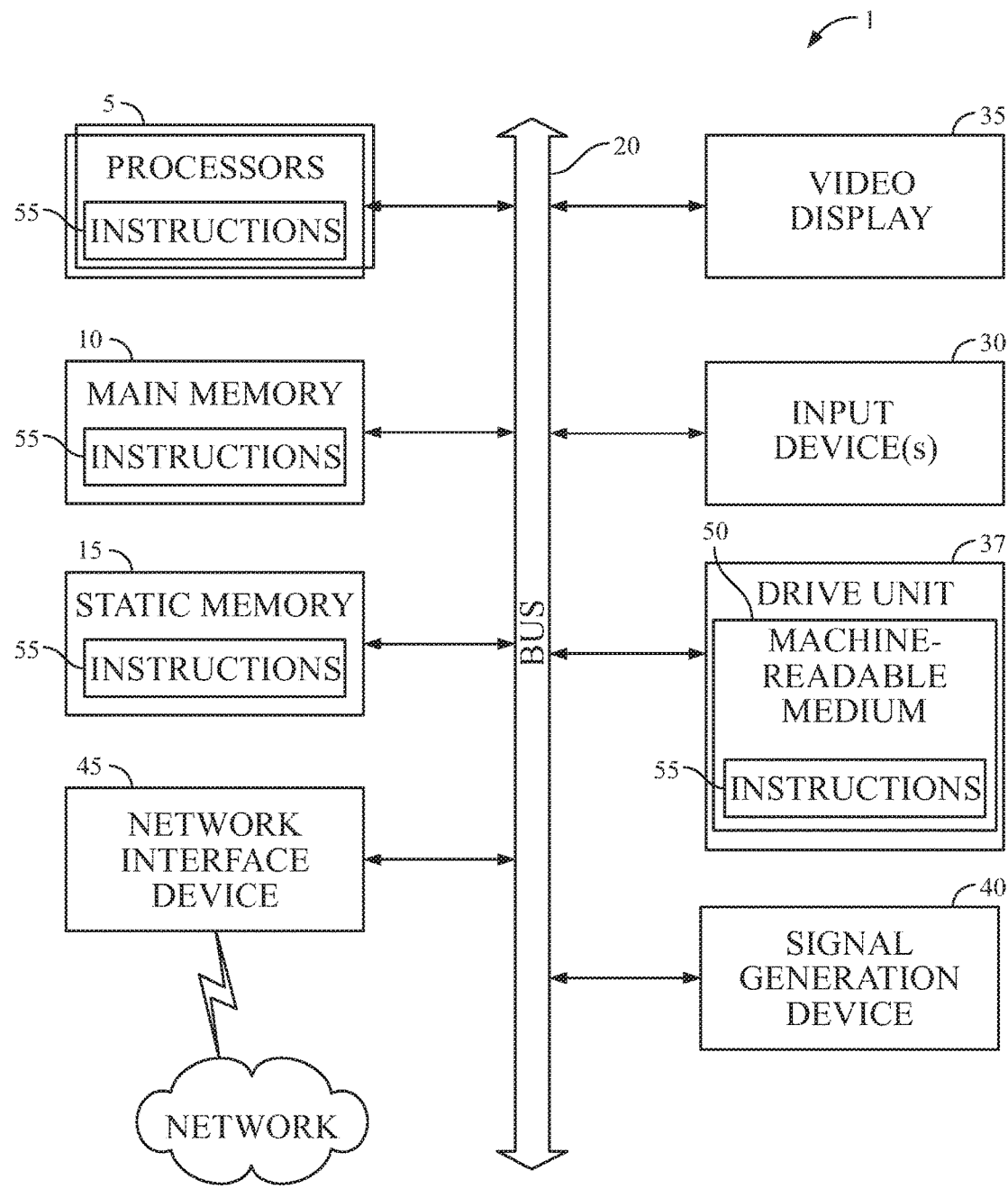
FIG. 10 is a schematic diagram of a computing system that is used to implement embodiments according to the present technology.

FIG. 10 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:
1. A device, comprising:
  four side panels connected together so as to form a tubular rectangle;
  a floor panel that covers an opening of the tubular rectangle, the floor panel comprising a raised test bed that receives a test medium;
  a top panel that comprising an optical lens that aligns with the raised test bed when the top panel covers another opening of the tubular rectangle;

the four side panels, the floor panel, and the top panel forming an optic chamber when joined together;
a light source that illuminates inside the device;
an illumination volume of the optic chamber; and
brackets disposed on each corner of the tubular rectangle, the brackets allowing for selective increasing or selective decreasing of the illumination volume based on placement of the lower panel in contact with a portion of the brackets.

2. The device according to claim 1, wherein each of the four side panels comprises angled ends, wherein the angled ends of adjacent ones of the four side panels are configured to interlock.

3. The device according to claim 1, further comprising a reflective material on a surface of the floor panel that is disposed inside the optic chamber.

4. The device according to claim 1, further comprising a reflective material on any of the top panel, the floor panel, the four side panels, a sidewall of the optical lens, and any combinations thereof.

5. The device according to claim 1, wherein the optical lens comprises any of macro lens or a colored lens.

6. The device according to claim 1, further comprising a calibration matrix disposed above the raised test bed.

7. The device according to claim 1, further comprising a second raised test bed that accommodates a second test medium.

8. The device according to claim 1, wherein the light source is disposed around the optical lens inside the optic chamber.

9. The device according to claim 8, wherein the light source comprises light emitting diode elements.

10. A system comprising:
an optical chamber device comprising:
four side panels connected together so as to form a tubular rectangle;
a floor panel that covers an opening of the tubular rectangle, the floor panel comprising a raised test bed that receives a test medium;
a top panel that comprising an optical lens that aligns with the raised test bed when the top panel covers another opening of the tubular rectangle;
the four side panels, the floor panel, and the top panel forming an optic chamber when joined together; and
a light source that illuminates inside the optical chamber device; and
a computing device comprising a processor and memory, the processor executing instructions stored in the memory to:
receive a selection of a test from an application;
based on the test, select a testing protocol;
receive an image of the test medium obtained through use of the optical chamber device; and
process the image with the testing protocol to obtain a test result,
the image being processed by:
applying a template outline that comprises a pre-determined field that aligns with the test medium, prior to receiving the image;
detecting a control line on the test medium;
identifying corners of the test medium that define test medium coordinates;
assigning values to each of red, green, blue, and gray colors in the test medium coordinates;
displaying an array of bars below the control line based on the assigned values;
wherein a bar in the array is identified as a test line when the bar has an increasing value compared to an adjacent bar.

11. The system according to claim 10, wherein the image comprises both the test medium and a calibration matrix.

12. The system according to claim 11, wherein the processor further executes instructions stored in the memory to self-calibrate using the calibration matrix in the image.

13. The system according to claim 10, further comprising adjusting the array using calibration information.

14. The system according to claim 13, wherein the calibration information is determined by:
locating a largest bar of the array, which constitutes a darkest level control line;
analyzing the bars to determine a set of shortest bars;
ranking the bars according to size;
calculating a detection threshold as a difference between the longest bar and the set of shortest bars, wherein a shortest of the set of shortest bars establishes a lightest level; and
storing the set of shortest bars for use as the calibration information.

15. The system according to claim 13, further comprising generating a graphical representation of the array.

16. A system comprising:
an optical chamber device comprising:
four side panels connected together so as to form a tubular rectangle;
a floor panel that covers an opening of the tubular rectangle, the floor panel comprising a raised test bed that receives a test medium;
a top panel that comprising an optical lens that aligns with the raised test bed when the top panel covers another opening of the tubular rectangle;
the four side panels, the floor panel, and the top panel forming an optic chamber when joined together;
a calibration matrix disposed adjacent to the raised test bed;
a light source that illuminates inside the optical chamber device;
an illumination volume of the optic chamber; and
brackets disposed on each of the corners of the tubular rectangle, the brackets allowing for selective increasing or selective decreasing of the illumination volume based on placement of the lower panel in contact with a portion of the brackets; and
a computing device comprising a processor and memory, the processor executing instructions stored in the memory to:
receive a selection of a test from an application;
based on the test, select a testing protocol;
receive an image of the test medium obtained through use of the optical chamber device;
apply a calibration profile for an image capturing device, the calibration profile being created from an image of the calibration matrix obtained using the image capturing device; and
process the image with the testing protocol to obtain a test result.

* * * * *

UNITED STATES PATENT AND TRADEMARK OFFICE
CERTIFICATE OF CORRECTION

PATENT NO.        : 9,983,117 B1
APPLICATION NO.   : 15/611726
DATED             : May 29, 2018
INVENTOR(S)       : Martin O'Connor Page 1 of 1

It is certified that error appears in the above-identified patent and that said Letters Patent is hereby corrected as shown below:

In the Specification

In Column 6, Line 43:
The phrase "generally includes a step 600 of" should read "generally includes a step of".

In Column 8, Line 43:
The phrase "increase of RGDG values" should read "increase of RGBG values".

In the Claims

In Column 13, Line 22 (Claim 5):
The phrase "comprises any of macro lens" should read "comprises any of a macro lens".

Signed and Sealed this
Second Day of August, 2022

*Katherine Kelly Vidal*

Katherine Kelly Vidal
*Director of the United States Patent and Trademark Office*